US008652025B2

(12) United States Patent
Laufer et al.

(10) Patent No.: US 8,652,025 B2
(45) Date of Patent: Feb. 18, 2014

(54) METHODS AND DEVICES FOR DIASTOLIC ASSIST

(76) Inventors: Michael D. Laufer, Menlo Park, CA (US); Freddy Abnousi, San Carlos, CA (US); Celina Yong, San Carlos, CA (US)

(*) Notice: Subject to any disclaimer, the term of this patent is extended or adjusted under 35 U.S.C. 154(b) by 10 days.

(21) Appl. No.: 13/277,158

(22) Filed: Oct. 19, 2011

(65) Prior Publication Data
US 2012/0296153 A1    Nov. 22, 2012

Related U.S. Application Data

(60) Provisional application No. 61/394,759, filed on Oct. 19, 2010, provisional application No. 61/478,495, filed on Apr. 23, 2011, provisional application No. 61/504,641, filed on Jul. 5, 2011.

(51) Int. Cl.
*A61N 1/362* (2006.01)
(52) U.S. Cl.
USPC .............................. 600/18; 128/898
(58) Field of Classification Search
USPC .............................. 600/18; 128/898
See application file for complete search history.

(56) References Cited

U.S. PATENT DOCUMENTS

| 6,651,670 B2 * | 11/2003 | Rapacki et al. ............... 128/898 |
| 6,971,998 B2 * | 12/2005 | Rosenman et al. ............. 604/57 |
| 7,186,210 B2 * | 3/2007 | Feld et al. ...................... 600/16 |

FOREIGN PATENT DOCUMENTS

| EP | 0515867 | 7/1999 |
| EP | 0949884 | 12/2005 |
| WO | WO 01/10287 | 2/2001 |

OTHER PUBLICATIONS

Abstract Session 23: Catheter Ablation: Atrial Tachycardia, Naspe Abstracts, Pacing and Clinical Electrophysiology, vol. 17, pp. 774-775, Apr. 1994, Blackwell Publishing.
Abstract Session 41: Ablation Vi: New Techniques in Atrial Ablation, Pacing and Clinical Electrophysiology, vol. 18, pp. 856-857, Apr. 1995.
Baker, MD, Brett M. et al., Nonpharmacologic Approaches to the Treatment of Atrial Fibrillation and Atrial Flutter, Journal of Cardiovascular Electrophysiology, vol. 6, No. 10, Pt. II, pp. 972-978, Oct. 1995, From the Cardiovascular Division, Washington University School of Medicine, St. Louis, Missouri, US.
Bredikis, Jurgis J. et al., Surgery of Tachyarrhythmia: Intracardiac Closed Heart Cryoablation, Pacing and Clinical Electrophysiology, vol. 13, pp. 1980-1984, Dec. 1990, Part II, Kaunas Arrhythmia Surgery Center, Kaunas, Lithuania.
Cox, James L. et al., The surgical treatment of atrial fibrillation, The Journal of Thoracic and Cardiovascular Surgery, vol. 101, No. 3, pp. 402-405, Mar. 1991, Mosby-Year Book, Inc., St. Louis, Missouri, US.

(Continued)

*Primary Examiner* — Christopher D Koharski
*Assistant Examiner* — Michael Carey
(74) *Attorney, Agent, or Firm* — Levine Bagade Han LLP

(57) ABSTRACT

The devices and method described herein allow for therapeutic damage to increase volume in these hyperdynamic hearts to allow improved physiology and ventricular filling and to reduce diastolic filling pressure by making the ventricle less stiff. For example, improving a diastolic heart function in a heart by creating at least one incision in cardiac muscle forming an interior heart wall of the interior chamber where the at least one incision extends into one or more layers of the interior heart wall without puncturing through the interior heart wall and the incision is sufficient to reduce a stiffness of the interior chamber to increase volume of the chamber and reduce diastolic filing pressure.

23 Claims, 8 Drawing Sheets

(56) References Cited

OTHER PUBLICATIONS

Cox, James L. et al., The surgical treatment of atrial fibrillation, II. Intraoperative electrophysiologic mapping and description of the electrophysiologic basis of atrial flutter and atrial fibrillation, The Journal of Thoracic and Cardiovascular Surgery, vol. 101, No. 3, pp. 406-423, Mar. 1991, Mosby-Year Book, Inc., St. Louis, Missouri, US.
Cox, James L., The surgical treatment of atrial fibrillation IV. Surgical Technique, The Journal of Thoracic and Cardiovascular Surgery, vol. 101, No. 4, pp. 584-592, Apr. 1991, Mosby-Year Book, Inc., St. Louis, Missouri, US.
Cox, James L., The status of surgery for cardiac arrhythmias, Circulation, Journal of the American Heart Association, vol. 71, No. 3., pp. 413-417, Mar. 1985, American Heart Association, Dallas, TX, US.
Cox, James L., Atrial fibrillation I: A new classification system, The Journal of Thoracic and Cardiovascular Surgery, vol. 126, No. 6, pp. 1686-1692, Dec. 2003, Division of Cardiothoracic Surgery, Washington University School of Medicine, St Louis, Mo., US.
Cox, James L., Atrial fibrillation II: Rationale for surgical treatment, The Journal of Thoracic and Cardiovascular Surgery, vol. 126, No. 6, pp. 1693-1699, Dec. 2003, Division of Cardiothoracic Surgery, Washington University School of Medicine, St Louis, Mo., US.
Cox, James L., The central controversy surrounding the interventional-surgical treatment of atrial fibrillation, The Journal of Thoracic and Cardiovascular Surgery, vol. 129, No. 1, pp. 1-4, Jan. 2005, Division of Cardiothoracic Surgery, Washington University School of Medicine, St Louis, Mo., US.
Schaff, Hartzell V. et al., Cox-Maze Procedure for Atrial Fibrillation Mayo Clinic Experience, Seminars in Thoracic and Cardiovascular Surgery, vol. 12, No. 1, pp. 30-37, Jan. 2000, Mayo Clinic and Mayo Foundation, Rochester, MN, US.
Arcidi Jr., J.M. et al., Evolution of the Maze III Procedure: are Modifications Necessary?, Division of Thoracic and Cardiovascular Surgery, vol. 47, Supplement, pp. 362-364, 1999, LDS Hospital, Salt Lake City, Utah, US.
Gregori Jr., Francisco et al., Cox Maze Operation Without Cryoablation for the Treatment of Chronic Atrial Fibrillation, The Society of Thoracic Surgeons, vol. 60, pp. 361-364, 1995, Department of Surgery, State University of Londrina Medical School, Londrina, Parana Brazil.
Haissaguerre, MD., Michel et al., Radiofrequency Catheter Ablation in Unusual Mechanisms of Atrial Fibrillation: Report of Three Cases, Journal of Cardiovascular Electrophysiology, vol. 5, No. 9, Sep. 1994, pp. 743-751, From the Hôpital Cardiologique du Haut-Lévêque, Bordeaux-Pessac, France: and the Department of Medicine, University of Arizona College of Medicine, Tucson, Arizona, US.
Haissaguerre, MD., Michel et al., Successful Catheter Ablation of Atrial Fibrillation, Journal of Cardiovascular Electrophysiology, vol. 5, No. 12, Dec. 1994, pp. 1045-1052, From the Hôpital Cardiologique du Haut-Lévêque, Bordeaux-Pessac, France: and the Department of Medicine, University of Arizona College of Medicine, Tucson, Arizona, US.
Kosakai Yoshio, Treatment of Atrial Fibrillation Using the Maze Procedure: The Japanese Experience, Seminars in Thoracic and Cardiovasculary Surgery, vol. 12, No. 1, pp. 44-52, Jan. 2000, W.B. Saunders Company.
Lavergne, Th., Prunier L. et al., Transcatheter Radiofrequency Ablation of Atrial Tissue Using a Suction Catheter, Pacing and Clinical Electrophysiology, vol. 12, Inserm U 256 & 28, pp. 177-186, Jan. 1989, Part II, Paris, France.
Cox, James L. et al., Modification of the Maze Procedure for Atrial Flutter and Atrial Fibrillation, I. Rationale and surgical results, The Journal of Thoracic and Cardiovascular Surgery, Division of Cardiothoracic Surgery, vol. 110, No. 2, pp. 473-484, Aug. 1995, Department of Surgery, Washington University School of Medicine, Barnes Hospital, St. Louis, MO, US.
Cox, James L. et al., Modification of the Maze Procedure for Atrial Flutter and Atrial Fibrillation, II. Surgical technique of the maze III procedure, The Journal of Thoracic and Cardiovascular Surgery, Division of Cardiothoracic Surgery, vol. 110, No. 2, pp. 485-495, Aug. 1995, Department of Surgery, Washington University School of Medicine, Barnes Hospital, St. Louis, MO, US.
Handa, Nobuhiro et al., Outcome of Valve Repair and the Cox Maze Procedure for Mitral Regurgitation and Associated Atrial Fibrillation, The Journal of Thoracic Cardiovascular Surgery, vol. 118, No. 4, 1999, pp. 628-635, Mayo Clinic and Mayo Foundation, Rochester, Minnesota, US.
McCarthy, Patrick M. et al., The Cox-Maze Procedure: The Cleveland Clinic Experience, Seminars in Thoracic and Cardiovascular Surgery, vol. 12, No. 1, pp. 25-29, Jan. 2000, W.B. Saunders Company.
Cox, James L. et al., The Maze-III Procedure Combined with Valve Surgery, Seminars in Thoracic and Cardiovascular Surgery, vol. 12, No. 1, pp. 53-55, Jan. 2000, W.B. Saunders Company.
Arcidi, Joseph M. et al., The Maze Procedure: The LDS Hospital Experience, Seminars in Thoracic and Cardiovascular Surgery, vol. 12, No. 1, pp. 38-43, Jan. 2000, W.B. Saunders Company.

\* cited by examiner

METHODS AND DEVICES FOR DIASTOLIC ASSIST

CROSS-REFERENCE TO RELATED APPLICATIONS

This application is a non-provisional of U.S. Provisional Application Nos. 61/394,759 filed on Oct. 19, 2010; 61/478,495 filed on Apr. 23, 2011; and 61/504,641 filed on Jul. 5, 2011, the contents of which are incorporated herein by reference in its entirety.

BACKGROUND OF THE INVENTION

Congestive heart failure (CHF) in the United States has a prevalence of approximately 5.8 million people and an incidence of approximately 550,000 people annually. CHF is a rapidly growing medical problem. CHF can be categorized as either systolic heart failure (SHF) or diastolic heart failure (DHF). The estimated direct and indirect cost of CHF in the United States for 2009 is $37.2 billion. CHF is the primary reason for 12-15 million office visits and 6.5 million hospital days each year. CHF is also thought to be the cause of at least 20 percent of all hospital admissions among patients older than 65. Over the past decade, the rate of hospitalizations for heart failure has increased by 159 percent. About half of all patients with CHF have DHF. DHF has an annual mortality of ~10%.

FIG. 1 illustrates a cross sectional view of a representation of a heart 10. In a normally functioning heart, oxygenated blood enters the heart 10 via pulmonary veins 12 into the right atrium 14. During diastole the heart muscles relax allowing the left atrium 16 to fill with the oxygenated blood. During systole, the heart muscle contracts reducing the volume of the left atrium 16 and causing oxygenated blood to flow through the aortic valve 18 into the aorta 20 for circulation through the body.

The hearts of patients with diastolic dysfunction can contract normally or even with hyperdynamic function. However, in patients experiencing DHF, the part of the cardiac cycle that involves diastole is abnormal as the left ventricle cannot relax or expand sufficiently. The inability of the left ventricle to fully relax results in sub-optimal filling of the left ventricle with blood.

In particular, diastolic dysfunction is determined by two factors: 1) active myocardial relaxation, primarily affecting early diastole; or 2) passive elasticity or distensibility of the left ventricle, primarily affecting late diastole.

The abnormal filling of the ventricles in DHF results in limited cardiac output, especially during exertion. As a result, for any given ventricular volume in a heart with DHF, ventricular pressures are elevated, with backup in the circulatory system, leading to pulmonary congestion and edema identical to those seen in patients with SHF. Symptomatically, patients may immediately feel short of breath. This dysfunction can ultimately lead to multiorgan dysfunction and death.

There are currently no approved devices for diastolic dysfunction. Additionally, pharmaceutical intervention has not yet shown to improve outcomes in this population.

BRIEF SUMMARY OF THE INVENTION

The present disclosure includes devices and methods to increase volume in these hyperdynamic hearts to allow improved physiology and ventricular filling and to reduce diastolic filling pressure In a first variation, the disclosure includes a method of improving a diastolic heart function in a heart of a patient having diasastolic heart dysfunction. One variation of the method includes positioning a medical device within a body of the patient; advancing the medical device into an interior chamber of the heart; creating at least one incision in cardiac muscle forming an interior heart wall of the interior chamber without cutting through the interior heart wall, where the incision is sufficient to reduce a stiffness of the interior chamber to increase volume of the chamber and reduce diastolic filing pressure.

The above method can further include creating a plurality of incision. The plurality of incision can comprise at least one hole in the cardiac muscle or can comprise creating a plurality of incision.

Typically the method includes creating at least one incision without reducing the integrity of the cardiac muscle.

Access to the heart can occur via a vascular approach, an open surgical approach, or a thoroscopic approach. Furthermore, advancing the medical device can comprise advancing the medical device into the interior chamber of the heart via a transapical approach.

The devices used to create the therapeutic injury can include any devices selected from the group consisting of a blade, a mechanical cutting device, an electrosurgical device, and a laser device.

In some variations, the methods occur by inducing tachycardia of the heart. Furthermore, incisions can be created on an exterior of the heart and/or an interior of the heart.

The devices can be secured to cardiac muscle prior to or during creating the incision.

The methods and devices can also optionally deliver bioactive agent to at least one incision to modify the healing process of the cardiac muscle.

Another variation of the method includes a method of increasing blood flow in a diseased heart. One such example includes positioning a medical device within a body of the patient; advancing the medical device into an interior chamber of the heart; locating a target area of heart tissue; and creating at least one incision in cardiac muscle of the heart tissue to decrease the stiffness of the interior chamber to permit the interior chamber to increase in volume during diastole.

Another variation of the methods includes methods of increasing blood flow in a diseased heart by advancing a device within a left ventricle of the heart; implanting an elastic member within the left ventricle such that upon diastole the elastic member expands the left ventricle to increase a volume within the left ventricle so increase blood flow therein.

The elastic member can comprise a plurality of elastic members positioned in a substantially concentric pattern within the left ventricle. Alternatively, or in combination, the elastic member can comprise at least one spirally shaped elastic member positioned in a substantially concentric pattern within the left ventricle.

In another variation the method can include an elastic member that is fluidly coupled to an expandable balloon member containing a fluid that is flowable between the balloon system and the elastic member, where contraction of the left ventricle applies a force to the elastic member driving fluid into the expandable balloon member and where upon diastole of the heart, the resiliency of the expanded balloon member drives the fluid into the elastic member to apply a force to a wall of the left ventricle to increase a volume of the left ventricle.

DETAILED DESCRIPTION OF THE INVENTION

The illustrations described herein are examples of the invention. Because of the scope of the invention, it is specifically contemplated that combinations of aspects of specific embodiments or combinations of the specific embodiments themselves are within the scope of this disclosure.

As noted above, the methods described herein increase a volume of a chamber of a heart to improve blood flow in diastolic heart failure. For example, incisions, cuts, holes, or other separation of tissue can be made in muscle forming the wall of the left ventricle to improve a diastolic function of the heart. Although the description and claims described herein discuss primarily treatments occurring in a left ventricle, unless specifically discussed or claimed, the treatments can occur in any chamber of the heart (e.g., the atriums and/or ventricles). Typically, access to the chambers of the heart (endocardium) can be made percutaneously or via a transapical approach. Once in the ventricle, small cuts, holes, or a combination thereof are made to the cardiac muscle at one or more layers of the musculature. In those cases where the outside of the heart is therapeutically damaged, access to the outside of the heart (i.e., the pericardium) can be obtained though a minimally invasive thoracotomy, stiff needle/catheter transapical approach, or sternotomy. The intervention can also be performed in any cardiac chamber or vascular entity The goal of the therapeutic damage is to increase volume in these hyperdynamic hearts to allow improved physiology and ventricular filling and to reduce diastolic filling pressure by making the ventricle less stiff. In some cases, the type of therapeutic damage, e.g., angles, dimensions, length, depth, density, and architecture shall balance of the integrity of the musculature versus the functional result. In many cases, the treatment can be optimized to ensure adequate function physiologically, hemodynamically, and electrophysiologically. Unless otherwise specified, the therapeutic treatments only extend into one or more layers of the cardiac muscle and not through the wall of the heart.

The therapeutic damage caused to the cardiac muscle can be additionally treated with agents that prevent closure of the wounds. Such agents can include pyrolitic carbon, titanium-nitride-oxide, taxanes, fibrinogen, collagen, thrombin, phosphorylcholine, heparin, rapamycin, radioactive 188Re and 32P, silver nitrate, dactinomycin, sirolimus, everolimus, Abt-578, tacrolimus, camptothecin, etoposide, vincristine, mitomycin, fluorouracil, or cell adhesion peptides. Taxanes include, for example, paclitaxel, 10-deacetyltaxol, 7-epi-10-deacetyltaxol, 7-xylosyl-10-deacetyltaxol, 7-epi-taxol, cephalomannine, baccatin III, baccatin V, 10-deacetylbaccatin III, 7-epi-10-deacetylbaccatin III, docetaxel. Additionally, implantable hardware or dug eluting device can be positioned within, near, or around, the area of the therapeutic damage.

Figure 1:
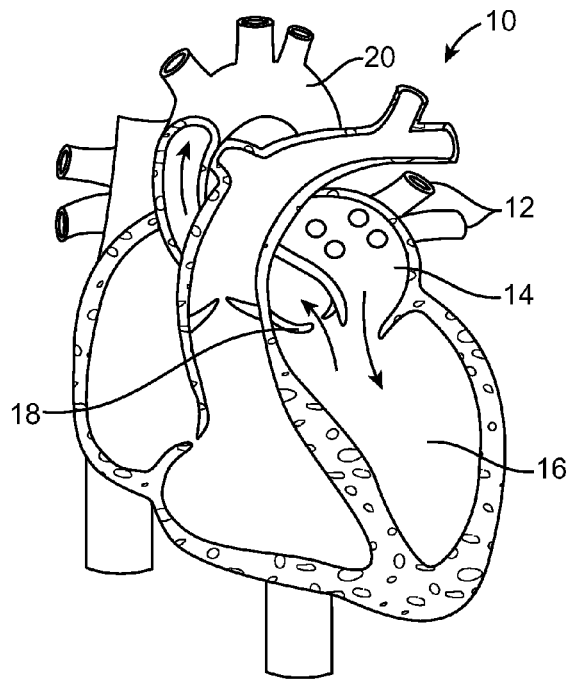
FIG. 1 illustrates a partial sectional view of a heart showing blood flow from the pulmonary veins into a left atrium.
Figure 2:
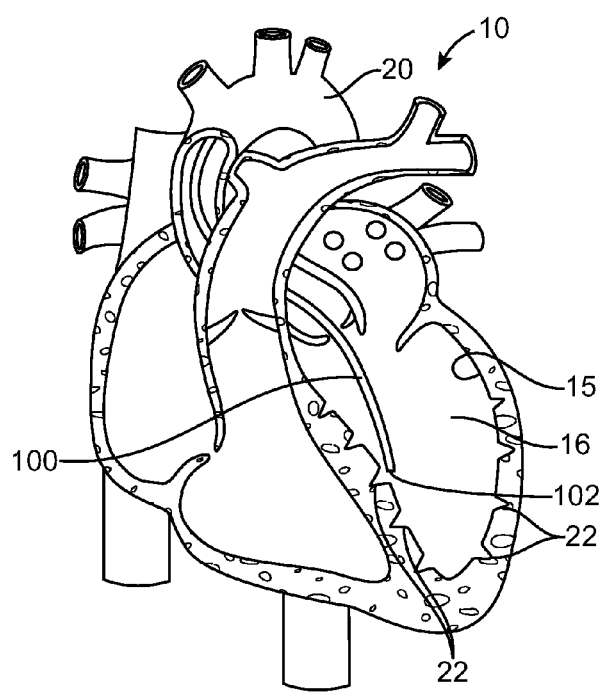
FIG. 2 illustrates one example of therapeutic damage to a chamber in the heart.

FIG. 2, illustrates a first example of a treatment according to the present disclosure. As shown, a physician advances a treatment device 100 into a chamber of the heart 10. Once inside the chamber, in this example the left ventricle 16, the physician can create one or more therapeutic incisions, cuts, cores, holes, or other similar therapeutic damage 22 to increase volume in the ventricle when in diastole. As noted above, this damage 22 reduces the stiffness of the ventricle (or cardiac muscle in the wall) to improve ventricular filling and reduce diastolic filling pressure (which resists blood flow into the ventricle). The method includes making one or more therapeutic damage sites 22 within one or more chambers of the heart. In this variation, the treatments 22 occur in the endocardium 15. Any of the treatment devices 100 described herein can include spring biasing, steering, a steerable sheath or catheter, a pull wire, or other mechanism to assist in navigation or apposition of the working end 102 of the device 100 against the target site.

Figure 3:
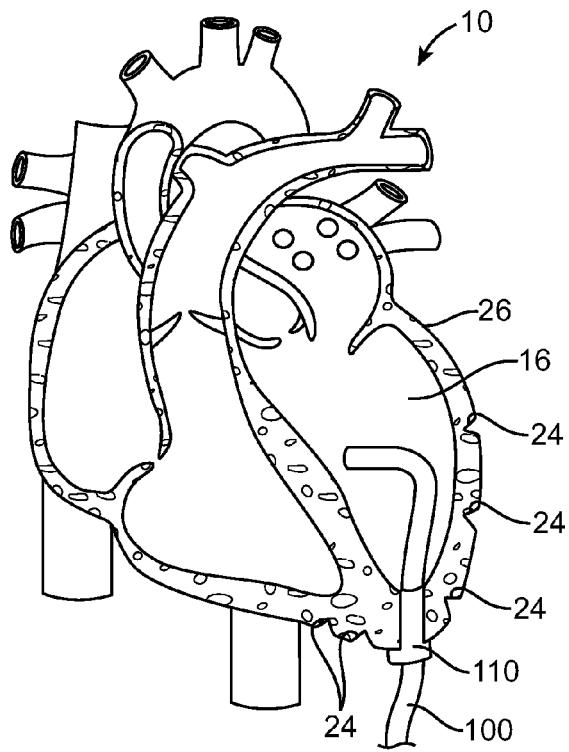
FIG. 3 illustrates another example of therapeutic damage to a chamber in the heart via an apical approach.
Figure 4:
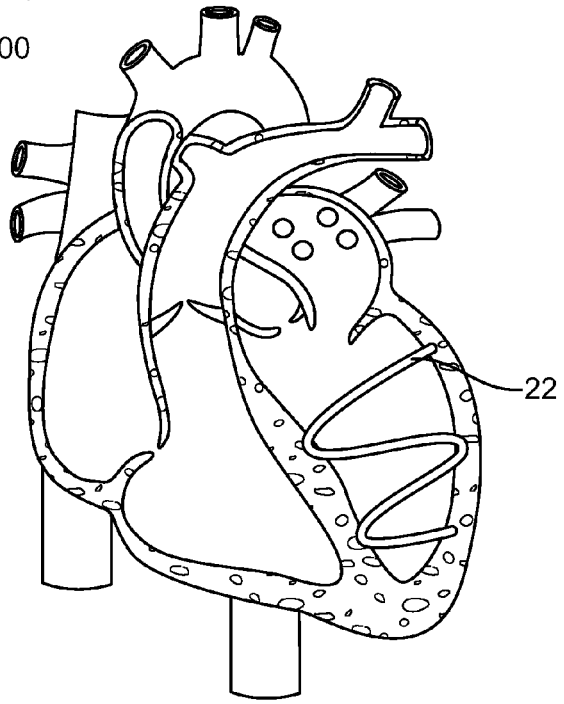
FIG. 4 illustrates therapeutic damage to a chamber in the heart formed via a patterned lesion.

FIG. 3 illustrates another variation of the treatment. In this example, the treatment sites 24 take place on an epicardium 26 of the heart 10. The figure also illustrates an optional transapical approach to access the atrium 16. The transapical access approach can include one or more ports 110 through which the physician positions the device 100 in the desired chamber. FIG. 4 illustrates another type of therapeutic incision 22. In this case, the incision comprises a helical or extended incision or a series of cuts along a particular pattern (e.g., a circular pattern around the atrium, a helical pattern, a zig-zag pattern, etc.). Such a pattern can include a continuous incision or a series of contiguous incisions, or even a combination of continuous and discrete incisions.

Figure 5A:
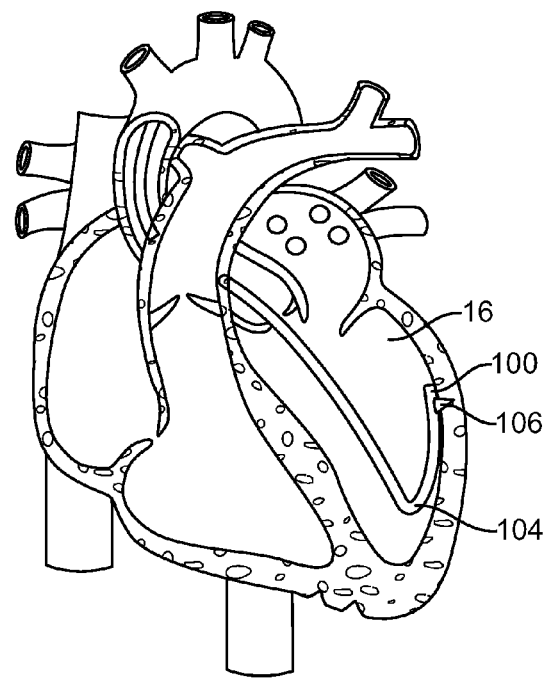
FIG. 5A shows another variation of a device inserted into a left atrium where the device includes a biased portion that drives a working end to the desired target site.

Devices for use in the methods described herein can incorporate alternative design options to improve safety to critical structures and to ensure cuts are made as expected (any combination or singular use of the below may be incorporated with any of the variations of the methods or devices discussed herein.) FIG. 5A shows another variation of a device 100 inserted into a left atrium 16. In this variation, the device 100 includes a biased portion 104 that drives a blade 106 or other portion of a working end of the device 100 to the desired target site. The biased portion 104 can comprise a j-shape with a spring to allow the spring to exert force on the wall of the heart to ensure a cut of the proper depth is made. The device 100 can also allow for a changed leverage point to allow for flexing at various distances from the tip of the blade. This allows for increased force at the blade tip due to greater leverage, as well as possibly allowing for catheter to be in contact with the opposite wall of the heart, thus also providing more force for the incision.

Additionally, a guide wire with various thickness and flexibility that can be maneuvered can be used to direct the device 100. The wire/obturator may also have a predetermined and engineered shape, made out of a memory shape alloy such as nitinol, such that it is inserted into the cutting catheter lumen after it is placed into the ventricle, once the transition temperature is reached, the shaped wire shapes the device 100 into a position that facilitates cutting.

Variations of the methods described herein can involve access from the femoral or other artery, traversing the natural curve of the aortic arch, with a tendency of the device 100 to straighten, thereby driving the cutting element into the ventricular wall, and allowing the device 100 and cutter to bias against the ventricular wall as it cuts. Specifically for the left ventricle 16, the device 100 can optionally have a bend that is angled mildly in the opposite direction as the aortic arch, ensuring that once it is in the left ventricle it is pushed against its wall.

Figure 5B:
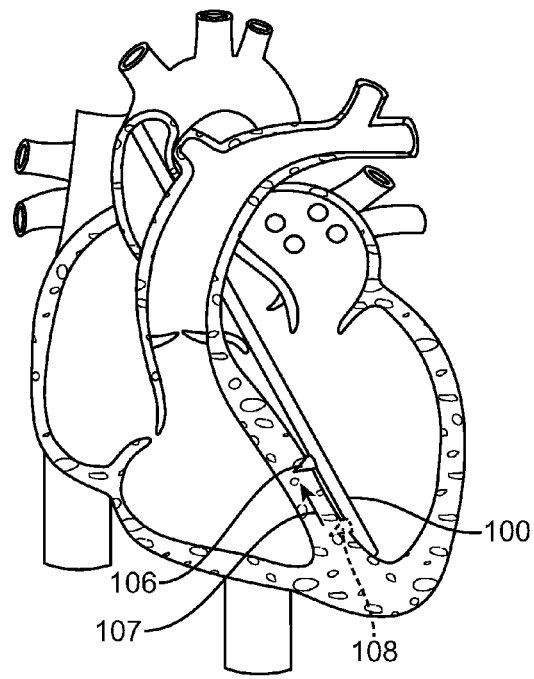
FIG. 5B illustrates another variation of a device having a slidable cutting portion that moves along path while the device remains stationary.

FIG. 5B illustrates another variation of a device 100 having a slidable cutting portion 106, 108 that moves along path 107 while the device 100 remains stationary. In one example, the device 100 can comprise a groove and tongue where the groove along a portion of the length of the device provides the path 107 along which the blade 106, 108 travels to make the incision.

Figure 6A:
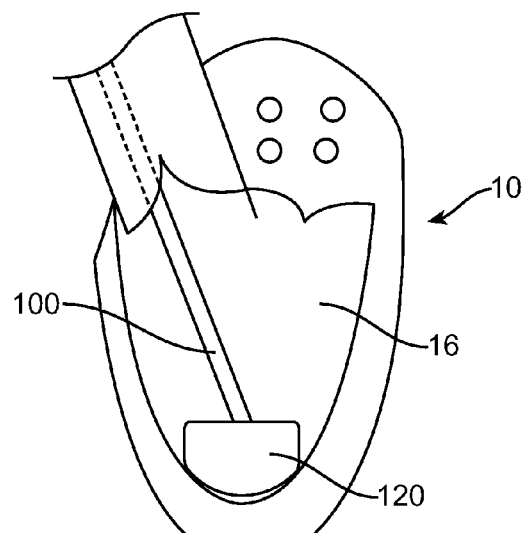
FIGS. 6A and 6B show another variation of a device incorporating a stabilizing member.
Figure 6B:
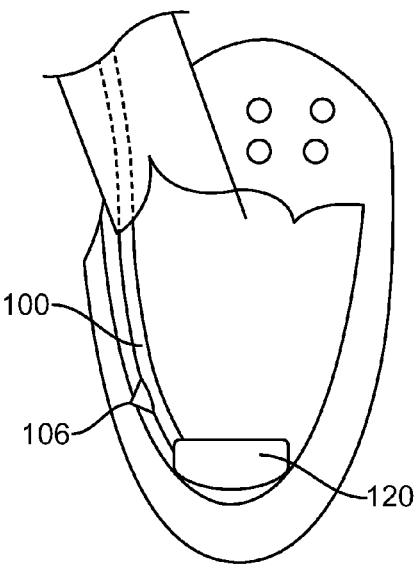

FIGS. 6A and 6B show another variation of a device 100 for providing treatment in accordance with this disclosure. As shown in FIG. 6A, a device 100 can include a stabilizer 120 that can optionally double as a cutter. In this variation, the cutting member 120 comprises a D type shapes that allow a physician to orient the device 100 and lock in to position. Doing so allows improves the ability of the physician to avoid key structures such as papillary muscles/valve during cuts while stabilizing the device 100 and optimizing the cuts. In the illustrated variation, the stabilizer 120 also serves as a cutter. In contrast, as shown in FIG. 6B, the stabilizer 120 can be used in conjunction with a cutting blade 106 or another means of creating an incision (e.g., an electrode, ultrasound transducer, blade, coring device, etc.) The stabilizer 120 can be positioned anywhere along the device 100. In alternate variations, the stabilizer is inflatable or expandable to assist in accessing the chamber of the heart.

Figure 6C:
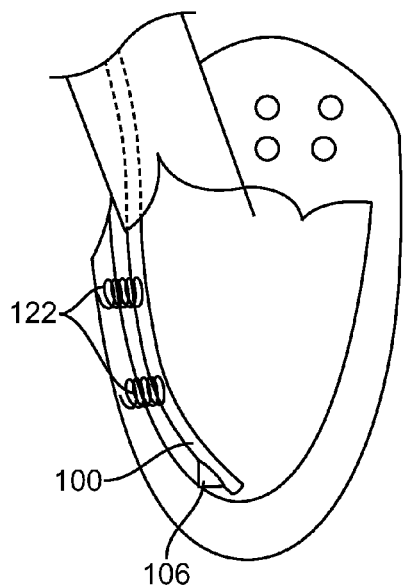
FIG. 6C illustrates a device having anchor members.

FIG. 6C illustrates another variation of a device including one or more hook or anchor members 122 that assist in maintaining the stability of the blade 106 or device 100 as it creates the incision in the wall. The anchor members 122 may or may not be part of the cutting blade 106 itself. In practice, the blade can enter tissue and pulled along the line of the cut. The blade would enter tissue but the anchor members 122 would make it difficult for the blade 106 to pull out of the tissue in a direction that is perpendicular to surface of tissue. The anchor members 122 can be actuatable or angled so that they release when pushed in a certain direction. The blade in this variation can be slidable as discussed above or simply pivot out of the device body.

In another variation, the blade can be used as a pacing electrode to permit tachycardic pacing during the procedure to ensure stability. The blade can pace at rate of 100-300 to increase time of muscle contraction which increases apposition of catheter with inner wall of heart. Cutting during systole allows linear longitudinal incisions to become curvilinear or spiral when heart is in diastole. Pacing can provide several functions. First, it can ensure contact between the blade and muscle, (i.e. if the knife isn't embedded, the heart rate cannot be paced due to the lack of an electrical circuit). Also, pacing can force the muscle onto the knife. The contraction of muscle can further assist in driving the blade into the muscle. Finally, if the heart is paced at a fast rate, the heart stays effectively contracted, allowing the user to make a cut without having to stop while the heart relaxes and then starts again.

Figure 7A:
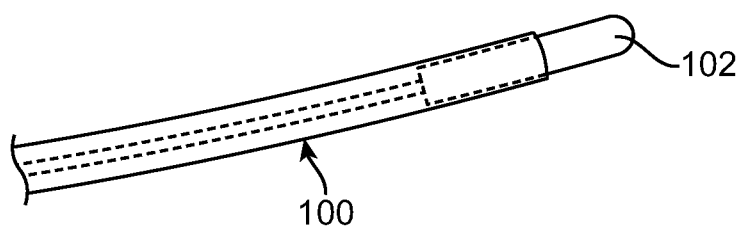
FIGS. 7A and 7B show a variation of a basic cutting device.
Figure 7B:
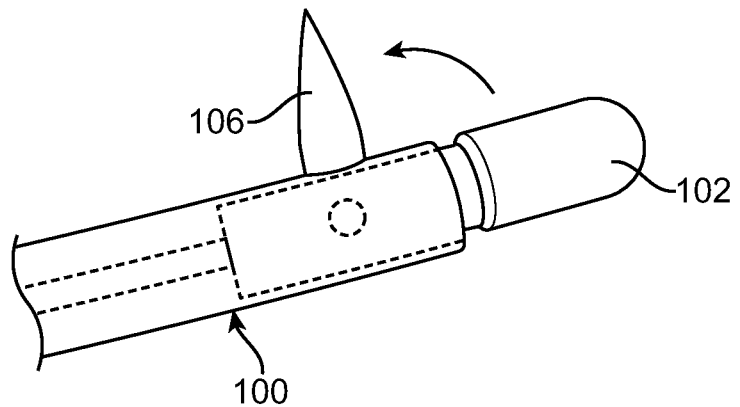
Figure 7C:
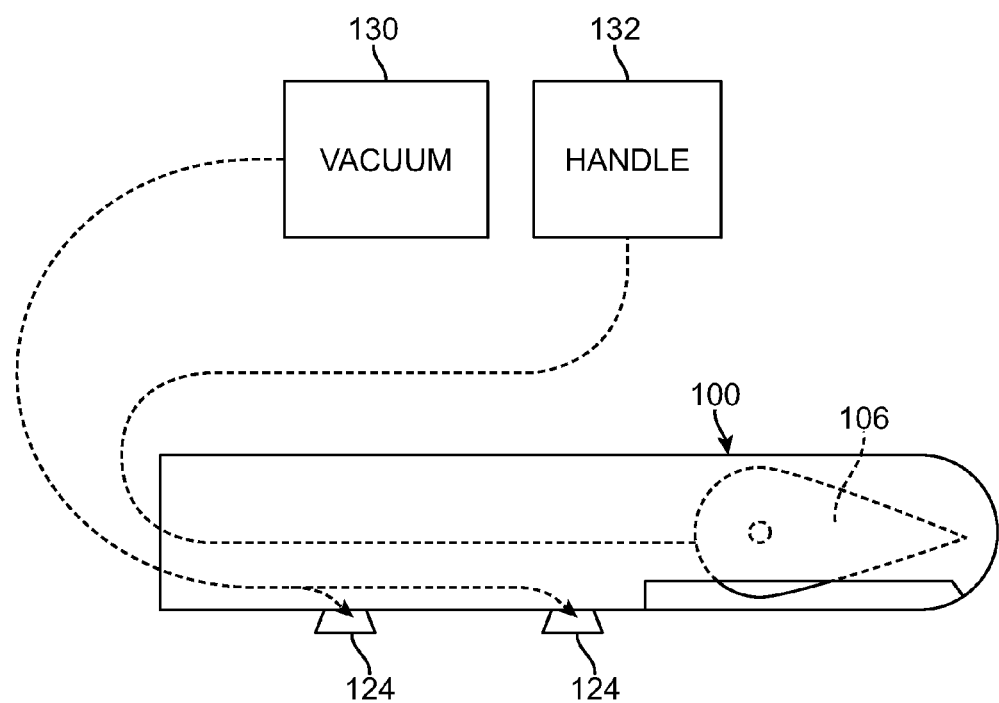
FIG. 7C illustrates another variation of a device having vacuum ports for attaching to tissue.

In one variation, the cutting apparatus is either a hard, sharp material with a knife-like edge that is delivered via catheter or other platform, or a laser such as those used in transmyocardial revascularization. FIG. 7A illustrates one example of a device 100 where a cutting blade (not shown) is withdrawn into the body of the device 100 to permit positioning of the device 100. As shown, the working end 102 can be atruamatic. Alternatively, the working end can include vision capabilities, or comprise a radiopaque material. FIG. 7B illustrates the blade 106 of the device 100 in an actuated position. As shown, in this variation, the blade 106 retracts in a swing arm fashion from the working end 102. Alternative variations of the device can replace the blade 106 with a coring device, an optical source for producing a laser, an electrode, or any other incision or hole creating means. FIG. 7C illustrates another variation of a device 100 including one or more vacuum ports 124 for coupling the working end of the device 100 to tissue. The vacuum ports 124 will be fluidly coupled to a source of vacuum 130 which can be adjacent to or coupled with a handle 132 of the device 100.

The knife like apparatus will be such that it can be deployed in a winging out manner, and structured such that catheter can be flexed with a pull wire or other system into the cardiac wall. Additionally, the knife will be designed to fall into a cardiac groove, and thus not impact the papillary muscles. The knife can be deployed and retracted into the failsafe position allowing the catheter to safely explore the cardiac chambers. The knife can be part of a tailor made catheter system or can be attached to the end of common catheters. The design may or may not allow for fluoro and exchange of other hardware while the knife is in place within the cardiac chambers. Additionally, the knife may be anchored to another portion of the heart, for example apex, with an anchoring device. Alternatively, the intervention may occur during induced tachycardia in order to ensure stability for intervention. On the other hand, if a laser is used it may be delivered through numerous fiber optic conduits or directly from a diode laser passed to the point of heart tissue where the treatment will be initiated. Of note, other technologies such as radiofrequency or cryothermy may be utilized as well.

The methods described herein can be performed using a number of additional modes to determine proper placement. For example, the methods can be performed under fluoroscopy and/or contrast agents. Alternatively, or in combination, a device can include a pressure sensing tip or along catheter at one or multiple points that determine when the device is positioned against the heart wall. In another variation, the device can include an opening at the distal end that is attached to arterial sensing equipment. Next, the waveform of a pressure wave is observed. When the hole is covered by tissue, the tissue blunts the waveform. This effect can be used as a test for catheter wall apposition. A physician can also confirm placement using an echocardiogram (TTE, TEE, intracardiac) where image shows position of device relative to wall/tissue.

Current can also be used to determine blade contact with tissue. For example, a current can be placed through the tissue (through ekg or similar type electrochemical sensing). As the blade touches the tissue, a voltage change can be measured from the circuit completed by the blade's contact with tissue.

Additionally, implantable hardware within, near, or around these cuts/holes with drug eluting capability may be part of this procedure. As well, the hardware (knife or otherwise)

used to make the intervention on the cardiac chambers may be coated with drugs much like in drug coated balloon angioplasty.

Figure 8:
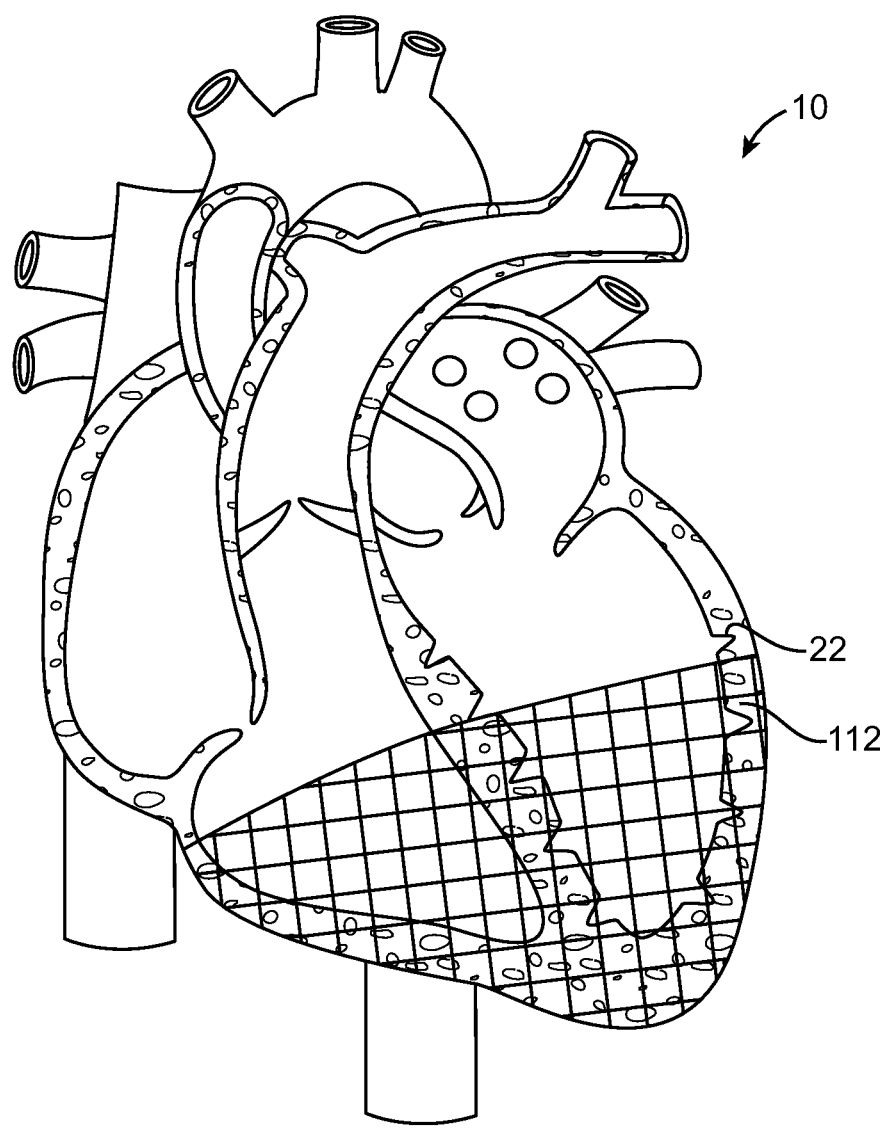
FIG. 8 shows another variation of the method described where a treated heart further includes an external wrapping material.

The devices described herein can be used in other applications as well. For example, the devices and methods can be used in treating hypertrophic cardiomyopathy (HCM). HCM is a condition in which the heart muscle becomes thick making it harder for blood to leave the heart. This thickening forces the heart to work harder to pump blood. The devices can be used to reduce subaortic tissue mass by cutting into the mass. The devices have application to make MAZE incisions by making multiple cuts in or around the pulmonary veins to interrupt conduction of atrial electrical activity. The devices and procedures can be used for commisurotomy, by cutting valve in various places including commisures to decrease valvular stenosis. The devices can be used for any and all cardiovascular structures that have undergone stenosis/sclerosis, such as renal arteries/pulmonary veins after RF exposure by cutting longitudinally with knife catheter. Furthermore, the devices can be used to perform plastys in all chambers of the heart by cutting longitudinally with the knife blade. Another potential use includes septal ablations by cutting longitudinally with the knife device. Endarterectomy using blade as cutting device to remove intima and plaque. This peeling/cutting device will be proximal to the distal umbrella unit at the tip of the device that is used to both peel plaque and prevent embolization. Current open methods of carotid endarterectomy lead to stenosis secondary to opening the vessel and subsequently closing the incision; our method would provide an advantage over this as we would not be opening the vessel. Glaucomaplasty via Canal of Schlem incision thus increasing the diameter of the canal, increasing the flow of aqueous humor, and thus decreasing intraocular pressures. The devices can be used for tear duct plasty as well as looking for chronic sinusitis; third ventriculoplasty for obstructive hydrocephalus; and psialalithiasis intervention to remove stones FIG. 8 shows another variation of the method described herein. In this example, the treated heart 10 includes an external wrapping material 112. Although the illustrated variation includes a partially wrap 112, the methods can include more or less wrapping. One of this extrinsic support 112 is to allow for the cardiac muscle to atrophy over time, creating extra volume in the ventricles of the hyperdynamic heart. Again, care will be taken not to make the wrap too limiting so as to impact physiology. Additionally, vital structures such as the coronary vessels will be accounted for and the device will be optimized in this procedure to ensure the correct physiology to avoid unintended damage to surrounding anatomy. The material forming the support 112 can be a wrapping material or an injectable material that provides support to the outside of the heart. The support 112 can be bioabsorbable or removable. For example, it can be comprised of hydroxyapatite or any other bioabsorbable material. The support 112 can also comprise shape memory alloy materials so that it is activated to reach its ideal dynamic properties at or near body temperature. In some variations, the portion of the heart 10 surrounded by the wrapping 112 can be limited to either/both ventricles and/or either/both atria. However, the support 112 can be customized to suit particular patient needs. Different versions of a support 112 can be replaced in a given patient over time, to better suit the patient's evolving cardiac condition over time. In additional variations, a given wrapping 112 can be adjustable, such that a follow-on procedure, either through a percutaneous or transapical approach, can adjust the wrap (e.g. inferior portion of wrapping tied tighter) to change its dimensions and qualities without requiring complete replacement.

Figure 9A:
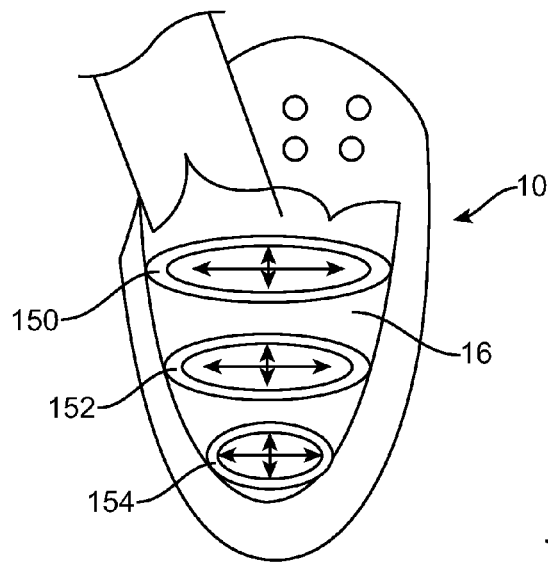
FIGS. 9A to 9C illustrate additional devices for use as diastolic assist devices (DAD).
Figure 9B:
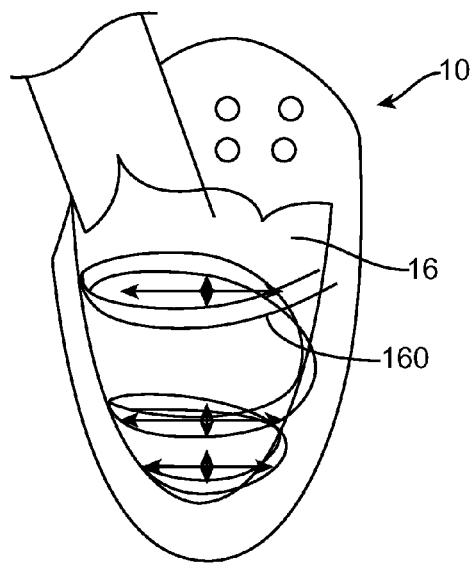
Figure 9C:
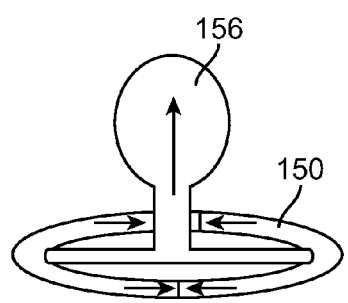

FIGS. 9A to 9C illustrate additional devices for use as diastolic assist devices (DAD). These devices can be used in conjunction with or in place of the above methods and devices. The diastolic assist devices can: assist in active relaxation of the left ventricle 16; assist in passive relaxation/elasticity of the left ventricle 16; provide a minimum necessary volume of the left ventricle 16 at elevated heart rates; provide improved pressure gradient into the left ventricle 16; unload LA during diastole preventing atrial dysfunction and pulmonary congestion; and/or provide a scaffolding for ventricular remodeling physically as well as through site directed drug elusion.

FIG. 9A shows a first version of a series of DAD devices 150, 152, 154. In this example, the DAD devices 150, 152, 154 comprise a series of concentric, elastic or inflatable substantially circular shaped device 150, 152, 154 that are inserted within the immediate interior perimeter of the left ventricle 16 in succession from the most inferior to the most superior circumference of the left ventricle through a noninvasive approach (or, alternatively via an apical approach). Variations of these devices can comprise any shape required to provide an effective diastolic assist (e.g., rectangular, oval, spiral, etc.) Placement of the DAD devices 150, 152, 154 can be positioned in any order and adjusted in any direction depending on the patient's specific requirements. The devices 150, 152, 154 may or may not have a spring-type component to them. These devices 150, 152, 154 may have the potential for drug elusion directly into any layer of the myocardium or within the left ventricle, of any pharmaceutical agent of choice. They may be constructed from any material currently used for cardiac catheters or a bioabsorbable material. The device will be adjusted to fit within the anatomical constraints in the left ventricle.

FIG. 9B illustrates another version of a DAD device 160. In this variation, the device 160 comprises a single elastic or inflatable shaped member that wraps concentrically in a spiral fashion within the left ventricle. The device 160 can be inserted via a noninvasive approach or as described above. The device 160 may or may not have a spring-type component to it. It can span up to the entire vertical height of the left ventricle to optimize diastole of the entire ventricle. However, alternate variations of the device 160 can include spans that are adjusted to optimize hemodynamics. The spirals can have any vertical distance (pitch) from each other to maximize diastolic function, and may be personalized to the patient's individual needs (for example, severity of diastolic function). This continuous device 160 can also have the potential for drug elusion to any layer of the myocardium or within the left ventricle, of any pharmaceutical agent of choice. It may be constructed from any material currently used for cardiac catheters or a bioabsorbable material. Variations of the device 160 will be adjusted to fit within the anatomical constraints in the left ventricle.

FIG. 9C illustrates another counterpulsation device 156 that can be used as an individual device or as a part of either diastolic assist device described above. This device 156 can the function of the diastolic assist device 150.

As shown, the device 156 comprises an expander bladder system that can be attached to another DAD device 150. Alternatively, the device 156 can be affixed to the inferior most point of the DAD 150, such that the lumen of the device 156 is continuous with the lumen of the DAD 150 system. Additionally, the bladder system 156 can be placed at the optimal hemodynamic point within the left ventricle by itself as well. The bladder system 156 is filled with a fluid such as saline or any other biologically compatible fluid. The balloon is designed to inflate and deflate in conjunction with the contraction of the left ventricle. That is, when the left ventricle contracts, it squeezes the DAD system 150 such that the luminal space of the catheter system decreases, resulting in pressure on the saline solution, displacing it into the counterpulsation balloon. This can be done by an overlapping DAD system 150, such that the perimeters overlap each other when the catheter system is compressed, resulting in a smaller overall lumen volume, or another similar method. Thus, fluid within the DAD 150 is displaced into the balloon lumen, inflating the balloon 156 during ventricular contraction, resulting in a lower left ventricular end-systolic volume.

When the left ventricle relaxes, then the DAD system 150 re-expands, re-increasing the luminal volume within the DAD system, consequently removing fluid from the counterpulsation balloon 156 by refilling the catheter system and emptying the balloon. This results in deflation of the balloon 156 during diastole, which not only increases the left ventricular end-diastolic volume, but also may cause a vacuum effect via negative pressure in the left ventricle, helping to pull more blood into the left ventricle from the left atrium during diastole. This can work in tandem with the DAD to help expand and fill the left ventricle during diastole.

We claim:

1. A method of improving a diastolic heart function in a heart of a patient having diastolic heart dysfunction, the method comprising:
    positioning a medical device within a body of the patient;
    advancing the medical device into an interior chamber of the heart; and
    creating at least one incision in cardiac muscle forming an interior heart wall of the interior chamber where the at least one incision extends into one or more layers of the interior heart wall without puncturing through the interior heart wall, where the incision is sufficient to reduce a stiffness of the interior chamber to increase volume of the chamber and reduce diastolic filing pressure.

2. The method of claim 1, where creating at least one incision comprises creating a plurality of incisions.

3. The method of claim 2, where the plurality of incisions comprise at least one hole in the cardiac muscle.

4. The method of claim 1, where creating at least one incision comprises creating a plurality of incision without reducing the integrity of the cardiac muscle.

5. The method of claim 1, where advancing the medical device comprises advancing the medical device into the interior chamber of the heart via a transapical approach.

6. The method of claim 1, where the medical device comprises a device selected from the group consisting of a blade, a mechanical cutting device, an electrosurgical device, a laser device, and a medical device including a retractable knife blade such that the knife blade can be refracted during positioning of the medical device.

7. The method of claim 1, further comprising inducing tachycardia of the heart.

8. The method of claim 1, further comprising creating at least one incision on an exterior surface of the heart.

9. The method of claim 1, further comprising securing a portion of the medical device to the cardiac muscle prior to or during creating the incision.

10. The method of claim 1, further comprising delivering a bioactive agent to at least one incision to modify the healing process of the cardiac muscle.

11. The method of claim 10, where delivering the bioactive agent comprises positioning a drug eluting device adjacent to or near to the incision.

12. A method of increasing blood flow in a diseased heart, the method comprising:
    positioning a medical device within a body of the patient;
    advancing the medical device into an interior chamber of the heart;
    locating a target area of heart tissue;
    creating at least one incision in cardiac muscle of the heart tissue, where the at least one incision only extends into one or more layers of the interior heart wall without puncturing through the interior heart wall, to decrease the stiffness of the interior chamber to permit the interior chamber to increase in volume during diastole.

13. The method of claim 12, where creating at least one incision comprises creating a plurality of incisions.

14. The method of claim 13, where the plurality of incisions comprise at least one hole in the cardiac muscle.

15. The method of claim 12, where creating at least one incision comprises creating a plurality of incisions without reducing the integrity of the cardiac muscle.

16. The method of claim 12, where advancing the medical device comprises advancing the medical device into the interior chamber of the heart via a transapical approach.

17. The method of claim 12, where the medical device comprises a device selected from the group consisting of a blade, a mechanical cutting device, an electrosurgical device, a laser device, comprises a medical device including a retractable knife blade such that the knife blade can be retracted during positioning of the medical device.

18. The method of claim 12, further comprising creating at least one incision on an exterior surface of the heart.

19. The method of claim 12, further comprising securing a portion of the medical device to the cardiac muscle prior to or during creating the incision.

20. The method of claim 12, further comprising delivering a bioactive agent to at least one incision to modify the healing process of the cardiac muscle.

21. The method of claim 10, where delivering the bioactive agent comprises positioning a drug eluting device adjacent to or near to the incision.

22. A method of improving a diastolic heart function in a heart of a patient having diastolic heart dysfunction, the method comprising:
    positioning a medical device within a body of the patient;
    advancing the medical device into an interior chamber of the heart;
    creating at least one incision in cardiac muscle forming an interior heart wall of the interior chamber where the at least one incision extends into one or more layers of the interior heart wall without puncturing through the interior heart wall, where the incision is sufficient to reduce a stiffness of the interior chamber to increase volume of the chamber and reduce diastolic filing pressure; and
    inducing tachycardia of the heart.

23. A method of increasing blood flow in a diseased heart, the method comprising:
    positioning a medical device within a body of the patient;
    advancing the medical device into an interior chamber of the heart;
    locating a target area of heart tissue;
    creating at least one incision in cardiac muscle of the heart tissue, where the at least one incision only extends into one or more layers of the interior heart wall without puncturing through the interior heart wall, to decrease the stiffness of the interior chamber to permit the interior chamber to increase in volume during diastole, and inducing tachycardia of the heart.

* * * * *